(12) United States Patent
Thorhauge

(10) Patent No.: US 8,951,482 B2
(45) Date of Patent: Feb. 10, 2015

(54) METHOD AND APPARATUS FOR THE SEPARATION OF A LIQUID FROM A GAS FEED STREAM IN A CATALYTIC REACTOR

(75) Inventor: Max Thorhauge, Herlev (DK)

(73) Assignee: Haldor Topsoe A/S, Lyngby (DK)

( * ) Notice: Subject to any disclaimer, the term of this patent is extended or adjusted under 35 U.S.C. 154(b) by 264 days.

(21) Appl. No.: 13/698,523

(22) PCT Filed: Jun. 17, 2010

(86) PCT No.: PCT/EP2010/003635
§ 371 (c)(1), (2), (4) Date: Nov. 16, 2012

(87) PCT Pub. No.: WO2011/144229
PCT Pub. Date: Nov. 24, 2011

(65) Prior Publication Data
US 2013/0066119 A1    Mar. 14, 2013

(30) Foreign Application Priority Data
May 20, 2010 (DK) ................................. 2010 00444

(51) Int. Cl.
*B01J 8/06* (2006.01)
*B01J 8/02* (2006.01)
*B01D 5/00* (2006.01)
*B01J 8/00* (2006.01)
*C07C 29/151* (2006.01)

(52) U.S. Cl.
CPC .. *B01J 8/025* (2013.01); *B01J 8/06* (2013.01); *B01D 5/0027* (2013.01); *B01D 5/009* (2013.01); *B01J 8/009* (2013.01); *B01J 8/0285* (2013.01); *B01J 8/0292* (2013.01); *B01J 2208/00132* (2013.01); *B01J 2219/32241* (2013.01); *C07C 29/1518* (2013.01)
USPC ............ 422/197; 210/773; 210/807; 261/128

(58) Field of Classification Search
CPC ........................................................ B01J 8/06
USPC .................... 422/197; 210/773, 807; 261/128
See application file for complete search history.

(56) References Cited

U.S. PATENT DOCUMENTS

| 5,266,281 A | 11/1993 | Kao et al. |
| 5,510,393 A | 4/1996 | Coffman |
| 2004/0198847 A1 | 10/2004 | Hojlund Nielsen et al. |
| 2008/0105416 A1 | 5/2008 | Katoh et al. |

FOREIGN PATENT DOCUMENTS

| CN | 1817435 A | 8/2006 |
| CN | 101173841 A | 5/2008 |
| JP | S504626 B2 | 2/1975 |
| WO | WO 2009/106232 A1 | 9/2009 |
| WO | WO 2009/118080 A1 | 10/2009 |

*Primary Examiner* — Elvis O Price
(74) *Attorney, Agent, or Firm* — Dickstein Shapiro LLP

(57) ABSTRACT

Method and apparatus for separating a liquid reaction product from a gaseous stream in a catalytic reactor by means of a metallic sheet being indirectly cooled by a cooling surface and having a plurality of percolations in form of geometric-shaped protrusions on both sides of the sheet each with an open base, the open base is on the side of the sheet facing a catalyst bed are arranged upwards and on the side facing the cooling surface the open base faces downwards.

15 Claims, 3 Drawing Sheets

METHOD AND APPARATUS FOR THE SEPARATION OF A LIQUID FROM A GAS FEED STREAM IN A CATALYTIC REACTOR

The present invention is related in general to separation of a liquid reaction product being formed by contacting a feed gas with solid catalyst packed as fixed beds in catalyst tubes.

In a number of catalytic processes it is advantageous to remove continuously the reaction product from the reacting feed gas in order to improve the equilibrium yield or the rate of the reaction towards the product, when removing a product from the gaseous phase to the liquid phase by condensation.

An example of such a reaction is the conversion of synthesis gas to methanol.

U.S. Pat. No. 5,262,443 describes a process for the preparation of methanol from synthesis gas at process conditions, where formed methanol product is removed from the gaseous phase by condensation of the methanol on the catalyst particles. By this process, the thermodynamic gas phase equilibrium boundary for methanol formation has been overcome and methanol yields approaching 100 percent in the catalyst bed effluent can be reached by once-through operation.

Condensation of liquid methanol on the catalyst particles has an adverse effect on the activity of the catalyst particles.

WO patent application no. 2009/106232 discloses an improved catalytic method and reactor for the production of methanol, wherein methanol as it is formed is removed from the gaseous phase into the liquid phase without reducing the catalyst activity of the catalyst. By the method and reactor of this patent application temperature of a liquid cooling agent being in indirect contact with the catalyst particles and a specific ratio of catalyst bed volume to a cooling surface is adjusted so that condensation of the methanol reaction product takes place for the most at the cooling surface.

In general, it is desirable to prevent condensation of liquid on catalyst particles in gaseous catalytic reactions, where the reaction product is removed from the gaseous phase into the liquid phase. Instead it is advantageous to allow condensation and transport of the liquid condensate outside the catalyst bed on a surface which has no or a reduced contact to the catalyst particles.

Accordingly, this invention is a method of separating a liquid reaction product from a gaseous stream in a catalytic reactor comprising the steps of:

in the reactor being provided with a fixed catalyst bed of solid catalyst particles arranging a cooling surface and a metallic sheet between the fixed bed and the cooling surface;

providing in the metallic sheet being indirectly cooled by the cooling surface a plurality of percolations in form of geometric-shaped protrusions on both sides of the sheet each with an open base, the open base is on the side of the sheet facing the catalyst bed arranged upwards and on the side facing the cooling surface the open base faces downwards;

condensing a gaseous reaction product being formed by reaction of the gaseous stream in the catalyst bed to the liquid reaction product on the metallic sheet and transferring the liquid reaction product through the open base facing upwards to the cooling surface; and passing the condensed liquid reaction product along the cooling surface and/or the metallic sheet and withdrawing the liquid reaction product from the bottom of the reactor.

The term "geometric-shaped protrusion" as mentioned hereinbefore and in the following description means a protrusion having a shape that obeys the laws of geometry.

When arranging a percolator in the form of a metallic sheet with protrusions and an open base pointing in upwardly direction on the side facing the catalyst bed in accordance with the invention, the side of the sheet being in contact with the catalyst particles and the gaseous stream will act as a liquid collector and transporter, whereas the opposite side acts as liquid rectifier. Thereby, detrimental redirection of the liquid reaction product into the catalyst bed is substantially avoided.

The term "upwards" and "downwards" as mentioned hereinbefore and in the following description means a direction pointing opposite to the direction of the gravity flow of the liquid reaction product and in the direction of the gravity flow, respectively.

In a preferred embodiment of the invention the geometric shape of the protrusions is a half pyramid, half cone or a semisphere, which provide an improved liquid rectifying effect.

In further a preferred embodiment of the invention the geometric-shaped protrusions on inner side of the sheet are adjoined at their open base to the geometric-shaped protrusions on outer side of the sheet so they share a common open base.

As mentioned above, the method of the invention is directed towards removal of a liquid phase from the gaseous phase mostly arising from condensation of a reaction product being formed by reaction of gaseous reactants in a fixed catalyst bed, so that the liquid phase is obtained outside the catalyst bed.

Catalytic reactions are frequently carried out in catalyst tubes. It is therefore preferred to form the metallic sheet tubular to fit the shape of the inner tubular wall of the catalyst tubes. The catalyst particles are then arranged on tube side, i.e. inside the tubular metallic sheet. In such an arrangement, the cooling surface will typically be the tube wall of the catalyst tubes, being then cooled by a cooling agent flowing on the outer wall of catalyst tubes.

In some catalytic reactions being carried out in a reactor vessel holding one or more catalyst beds within a common shell of the reactor it is preferred to arrange one or more metallic sheets according to the invention in form of a tube within the catalyst bed so that the catalyst particles surround the outer side of the tubular metallic sheet, which is then indirectly cooled by the cooling surface. The cooling surface is in such an embodiment preferably in tubular form and arranged on tube side, i.e. inside the tubular metallic sheet.

The invention further provides an apparatus being useful in the method according to the invention.

The apparatus according to the invention for separating a liquid reaction product from a gaseous stream in a catalytic reactor comprises:

a metallic sheet aligned to a cooling surface;

on both sides of the metallic sheet a plurality of percolations in form of geometric-shaped protrusions each with an open base, on the side of the sheet facing a catalyst bed within the catalytic reactor, the open base is arranged upwards and on the side facing the cooling surface the open base points downwards.

In a preferred embodiment of the apparatus of the invention, the geometric-shaped protrusions are in form of a half pyramid.

In still a preferred embodiment of the apparatus of the invention, the geometric-shaped protrusions are in form of a half cone.

In further a preferred embodiment of the apparatus of the invention, the geometric-shaped protrusions on inner side of the sheet are adjoined at their open base to the geometric-shaped protrusions on outer side of the sheet and share a common open base.

In a further preferred embodiment of the apparatus of the invention, the metallic sheet is in form of a tube.

It is further preferred that the cooling surface is in form of a tube.

In the following description the invention is described in more detail by reference to the drawings in which FIG. 1 is a perspective view of a section of a percolator in form of metallic sheet provided with protrusions according a specific embodiment of the invention;

Figure 1:
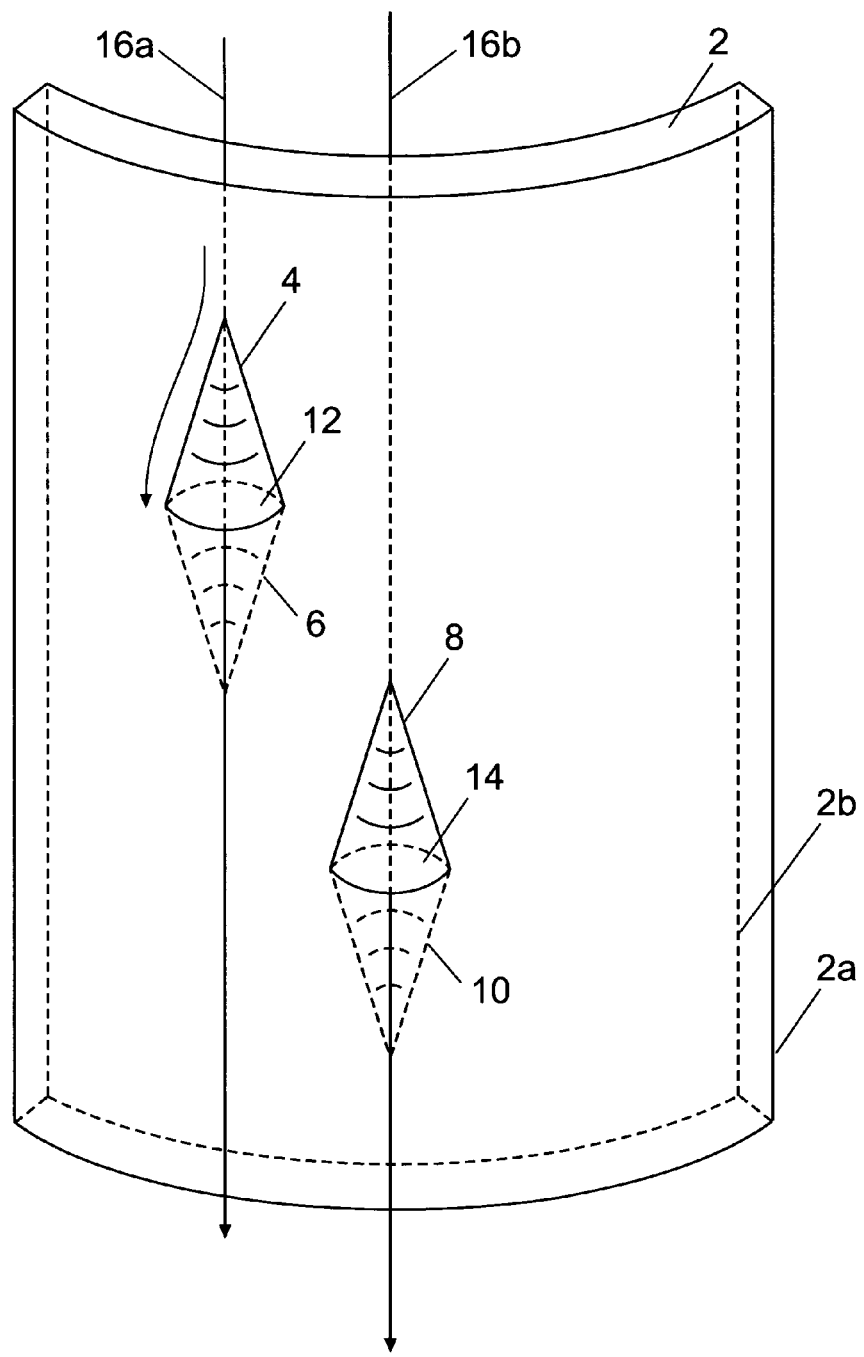

FIG. 1 shows a metallic sheet 2 for use in the method according to the invention being provided with percolations 4,6,8 and 10. The protrusions are formed as half cones on the front side 2a and back side 2b of sheet 2. Protrusions 4 and 8 protruding from the front side 2a, and protrusions 6 and 10 protruding from the back side 2b are adjoined and share a common open base 12 and 14, respectively. Catalyst particles (not shown) are arranged on back side 2b of the sheet. The tapered end of half cones 4 and 8 are on front side 2a directed upwards, i.e. in opposite direction of gravity flow of a liquid as shown by arrows 16a and 16b. On back side 2b the tapered end of half cones 6 and 10 direct downwards in the same direction as the gravity flow of the liquid. The part of the open base 12 and 14 protruding from back side 2b into the space with the catalyst particles points then into direction opposite to the liquid flow and functions as liquid collector and the part of the open base 12 and 14 is points into direction of the liquid flow and acts as liquid outlet on the front side 2a of sheet 2. Thus, a flow of liquid being condensed on the back (inner) side 2b is collected in open base 12 and 14 and passed to front side 2a.

Figure 2:
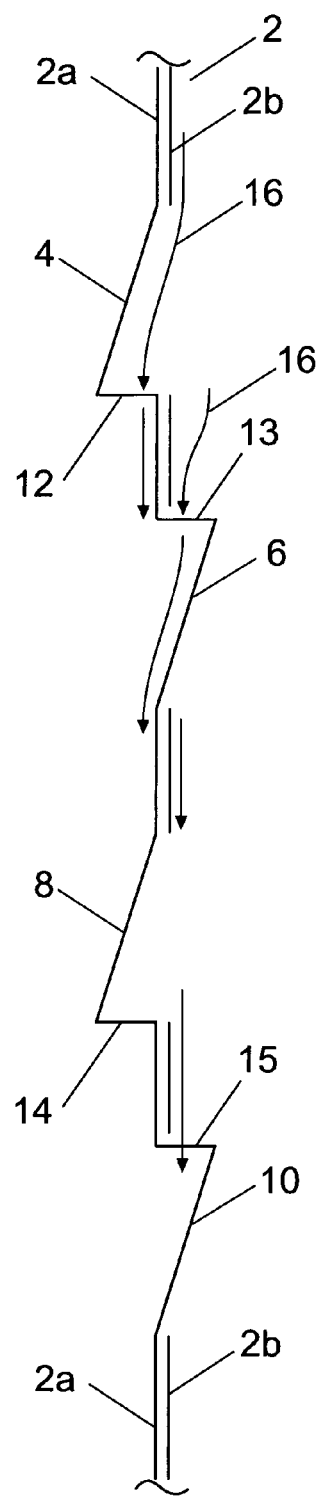
FIG. 2 is cross-sectional view of a section of a metallic sheet provided with protrusions according a specific embodiment of the invention for use in a catalyst tube.

FIG. 2 represents a cross-sectional view of a metallic sheet for use in a method according to the invention with percolations in form of half cone or half pyramid shaped protrusions 4,6,8,10 and open bases 12,13,14,15 alternately in upwards and downwards direction of the gravity flow 16 of a liquid. Catalyst particles (not shown) are arranged in the space facing the inner wall 2b of sheet 2. As indicated by arrows 16, a gaseous reaction product from a catalyst bed with the catalyst particles condenses on inner wall 2b and will be directed through the open bases 12,13,14,15 to outer wall 2a. A minor part of the gaseous product will also flow through the open bases and condenses then on the outer wall 2a and flows downwardly together with the liquid product stream along outer wall 2a towards bottom of the sheet.

Figure 3:
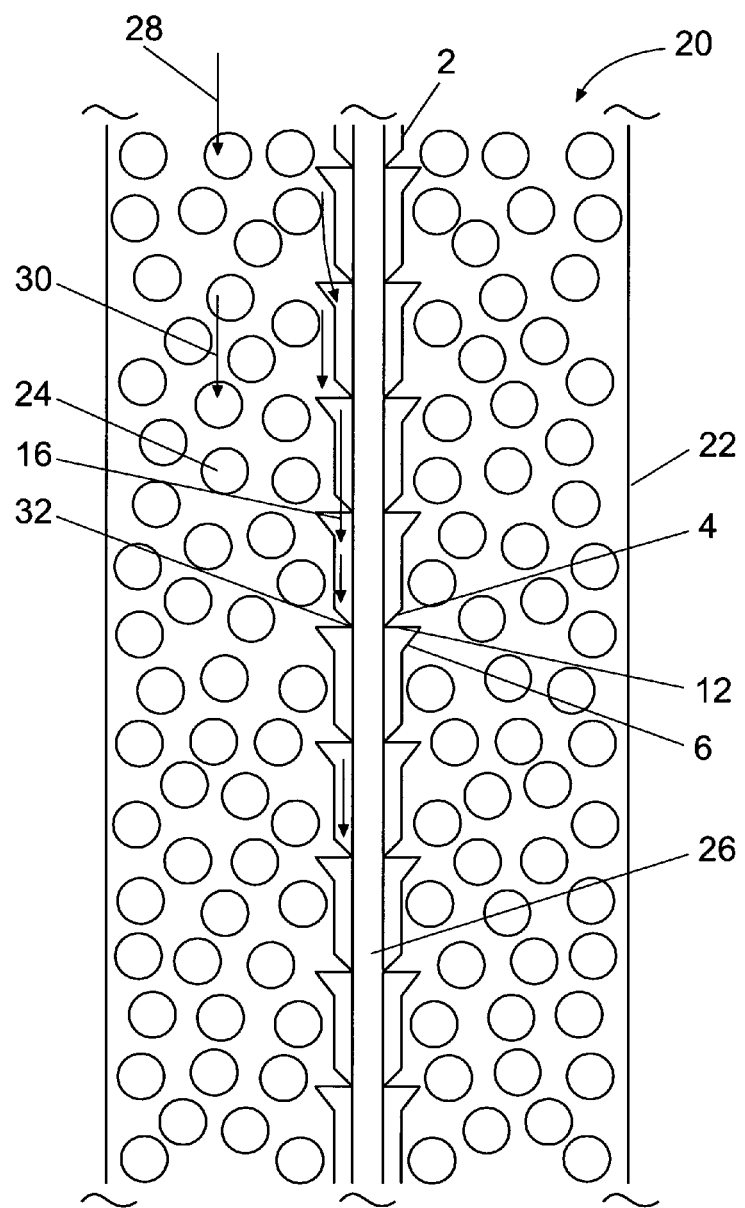
FIG. 3 shows a cross-sectional view of a reactor being provided with a number of percolators in form of metallic sheets according to a specific embodiment of the invention.

FIG. 3 is a catalytic reactor being provided with a number of metallic sheets (only one shown) within a catalyst bed according to an embodiment of the invention.

Reactor 20 holds within shell 22 a catalyst bed 24 with a plurality of catalyst particles. Metallic sheet 2 in form of a tube is arranged within the catalyst bed and surrounded by catalyst particles. Metallic sheet 2 is provided with a plurality of protrusion 6 and 4 sharing an open base as further shown in FIG. 1. The part of the common open base 12 facing the catalyst bed is directed opposite to the gravity flow of a condensed liquid reaction product 16 and the part of base 12 protruding from inner wall of sheet 2 is directed towards the liquid flow. Tubular sheet 2 is cooled by a cooling surface in form of a cooling tube 26. When operating reactor 20, a gaseous stream is passed through catalyst bed 24. In the catalyst bed the gaseous stream reacts to a gaseous product 30. Reaction product 30 is condensed mainly on outer wall of sheet tube 2 and forms liquid reaction product 32. The liquid reaction product when flowing along the outer wall of sheet tube 2 is collected by open bases 12 protruding towards the catalyst particles and transferred to the inner wall of sheet 2 through part of the open base 12 protruding from inner wall of the sheet tube towards cooling tube 26. Having been passed to the inner wall of tube sheet 2, the liquid reaction product flows along the inner wall and on the cooling tube to the bottom of reactor 2 and is withdrawn through an outlet (not shown) from the reactor.

The invention claimed is:

1. Method of separating a liquid reaction product from a gaseous stream in a catalytic reactor comprising the steps of:
   in the reactor being provided with a fixed catalyst bed of solid catalyst particles arranging a cooling surface and a metallic sheet between the fixed bed and the cooling surface;
   providing in the metallic sheet being indirectly cooled by the cooling surface a plurality of percolations in form of geometric-shaped protrusions on both sides of the sheet each with an open base, the open base is on the side of the sheet facing the catalyst bed arranged upwards and on the side facing the cooling surface the open base faces downwards;
   condensing a gaseous reaction product being formed by reaction of the gaseous stream in the catalyst bed to the liquid reaction product on the metallic sheet and transferring the liquid reaction product through the open base facing upwards to the cooling surface; and
   passing the condensed liquid reaction product along the cooling surface and/or the metallic sheet and withdrawing the liquid reaction product from the bottom of the reactor.

2. The method of claim 1, wherein the geometric-shaped protrusions are in form of a half pyramid.

3. The method of claim 1, wherein the geometric-shaped protrusions are in form of a half cone.

4. The method of claim 1, wherein the geometric-shaped protrusions are in form of a semisphere.

5. The method in accordance with claim 1, wherein the geometric-shaped protrusions on the inner side of the sheet are adjoined at their open base to the geometric-shaped protrusions on the outer side of the sheet and share a common open base.

6. The method in accordance with claim 1, wherein the metallic sheet is in form of a tube.

7. The method in accordance with claim 1, wherein the cooling surface is in form of a tube.

8. The method in accordance with claim 6, wherein the fixed catalyst bed is arranged on outer side of the tubular metallic sheet.

9. The method in accordance of claim 6, wherein the fixed catalyst bed is arranged on inner side of the tubular metallic sheet.

10. A reactor for separating a liquid reaction product from a gaseous stream comprising within the reactor:
   a metallic sheet;
   a cooling surface; and
   a catalyst bed, wherein
   the metallic sheet is aligned to the cooling surface, the metallic sheet is provided on both sides with a plurality of percolations in form of geometric-shaped protrusions each with an open base, on the side of the sheet facing the catalyst bed, the open base is arranged upwards and on the side facing the cooling surface the open base points downwards.

11. The reactor of claim 10, wherein the geometric-shaped protrusions are in form of a half pyramid.

12. The reactor of claim 10, wherein the geometric-shaped protrusions are in form of a half cone.

13. The reactor according to claim 10, wherein the geometric-shaped protrusions on the inner side of the sheet are adjoined at their open base to the geometric-shaped protrusions on the outer side of the sheet and share a common open base.

14. The reactor according to claim 10, wherein the metallic sheet is in form of a tube.

15. The reactor according to claim 10, wherein the cooling surface is in form of a tube.

* * * * *